US007939522B1

(12) United States Patent
Davis

(10) Patent No.: US 7,939,522 B1
(45) Date of Patent: May 10, 2011

(54) DOSAGE FORMULATIONS FOR ACETYLCHOLINESTERASE INHIBITORS

(76) Inventor: Bonnie M Davis, Syosset, NY (US)

( * ) Notice: Subject to any disclaimer, the term of this patent is extended or adjusted under 35 U.S.C. 154(b) by 0 days.

(21) Appl. No.: 09/856,282

(22) PCT Filed: Nov. 19, 1999

(86) PCT No.: PCT/US99/27481
§ 371 (c)(1),
(2), (4) Date: Jun. 18, 2001

(87) PCT Pub. No.: WO00/30446
PCT Pub. Date: Jun. 2, 2000

(51) Int. Cl.
*A61K 31/55* (2006.01)
(52) U.S. Cl. ....................................... 514/215
(58) Field of Classification Search ............... 514/219, 514/212.01, 215
See application file for complete search history.

(56) References Cited

U.S. PATENT DOCUMENTS

| | | | |
|---|---|---|---|
| 4,138,475 A | 2/1979 | McAinsh et al. | |
| 4,140,756 A | 2/1979 | Gallian | |
| 4,173,626 A | 11/1979 | Dempski et al. | |
| 4,193,985 A | 3/1980 | Bechgaard et al. | |
| 4,252,786 A | 2/1981 | Weiss et al. | |
| 4,663,318 A | 5/1987 | Davis | |
| 4,900,748 A * | 2/1990 | Brossi et al. | 514/411 |
| 5,051,261 A | 9/1991 | McGinity et al. | |
| 5,055,306 A | 10/1991 | Barry et al. | |
| 5,057,317 A | 10/1991 | Iida | |
| 5,068,111 A | 11/1991 | Lovrecich et al. | |
| 5,091,189 A | 2/1992 | Heafield et al. | |
| 5,151,273 A | 9/1992 | Korsatko-Wabnegg et al. | |
| 5,162,117 A | 11/1992 | Stupak et al. | |
| 5,213,811 A | 5/1993 | Frisbee et al. | |
| 5,283,065 A | 2/1994 | Doyon et al. | |
| 5,376,384 A | 12/1994 | Eichel et al. | |
| 5,407,687 A | 4/1995 | Coffin et al. | |
| 5,427,799 A | 6/1995 | Valentine et al. | |
| 5,445,829 A | 8/1995 | Paradissis et al. | |
| 5,462,747 A | 10/1995 | Radebaugh et al. | |
| 5,472,708 A | 12/1995 | Chen | |
| 5,519,017 A * | 5/1996 | Opitz | 514/215 |
| 5,585,375 A * | 12/1996 | Davis | 514/215 |
| 5,589,475 A | 12/1996 | Snorrason | |
| 5,643,905 A * | 7/1997 | Moormann | 514/215 |
| 5,668,117 A * | 9/1997 | Shapiro | 514/55 |
| 6,273,260 B1 | 8/2001 | ColDepietro et al. | |
| 6,565,883 B2 * | 5/2003 | Ogorka et al. | 424/474 |

FOREIGN PATENT DOCUMENTS

| | | |
|---|---|---|
| CA | 1325632 | 12/1993 |
| CA | 1 326 632 | 1/1994 |
| CA | 1326632 | 2/1994 |
| CA | 2 121 870 | 10/1994 |
| EP | 648771 A1 | 4/1995 |
| EP | 0 653 427 | 5/1995 |
| EP | 653 427 | 5/1995 |
| EP | 879 596 | 11/1998 |
| WO | 88/08708 | 11/1988 |
| WO | WO88/08708 | 11/1988 |
| WO | WO97/03987 | 2/1997 |
| WO | 98/22072 | 5/1998 |
| WO | WO99/21561 | 5/1999 |
| WO | 00/19985 | * 4/2000 |
| WO | 00/30446 | 6/2000 |
| WO | 00 38686 | 7/2000 |
| WO | 00/51970 | 9/2000 |

OTHER PUBLICATIONS

Conte et al., "Press-Coated Tablets for Time-Programmed Release of Drugs", Biomaterials, vol. 14, No. 13, pp. 1017-1023.*
Nordberg et al. Cholinesterase inhibitors in the treatment of Alzheimer's disease: a comparison of tolerability and pharmacology. Drug Safety, 1998, vol. 19, No. 6, pp. 465-480.*
Riemman et al. Influence of the cholinesterase inhibitor galanthamine hydrobromide on normal sleep. Psychiatry Research, 1994, vol. 51, No. 3, pp. 253-267) (Abstract attached).*
Faber et al. Am. J. Psychiatry, Jan. 1999, vol. 156, No. 1, p. 156.*
Kennedy et al. J. Clin. Invest., 1984, vol. 74, pp. 972-975.*
Conte, U, et al. Press-Coated Tablets for Time-Programmed Release of Drugs, Biomaterials. 1993, vol. 14, No. 13 pp. 1017-1023, Entire Document.
Goodman & Gilman's The Pharmacological Basis of Therapeutics, Ninth Edition, pp. 161-176. Chapter 8 (eds. Joel G. Hardman and Lee E. Limbird, McGraw-Hill, 1996).
Circadian Rhythms and Drug Deliver—Journal of Controlled Release, 16 (1991) 63-74.
Sensitive Liquid Chromatographic Method for Physostigmine in biological fluids using dual-electrode electrochemical Detection—Robin Whelpton & Thomas Moore—Journal of Chromatography 341 (1985) 361-371.
Pub Med—J. Clin Pharamacol, Mar. 29, 1989(3) 278-84—Single dose safety, tolerance and pharmacokinetics of HP 092 in healthy young men: a potential Alzheimer agent—Pur SK, Hsu RS, Ho I, Lassman HB.
Pub Med—J. Clin Pharamacol, Oct. 30, 1990(10) 948-55—Multiple doese pharmacokinetics, safety, and tolerance of velnarine (HP029) in healthy elderly subjects: a potential therapeutic agent for Alzheimer's disese—Puri SK, Ho I, Hsu R, Lassman HB.

(Continued)

*Primary Examiner* — James D Anderson
(74) *Attorney, Agent, or Firm* — Ladas & Parry LLP

(57) ABSTRACT

Acetylcholinesterase inhibitors are of use for treating a variety of diseases and conditions including Alzheimer's disease. They also affect circadian rhythms. In order to optimize the use of such compounds, the present invention provides dosage forms and methods of treatment wherein an effective amount of a centrally-acting acetylcholinesterase inhibitor is formulated so as to delay its activity for a predetermined period. Suitable acetylcholinesterase inhibitors include galanthamine, lycoramine, analogs thereof and rivastigmine.

32 Claims, No Drawings

OTHER PUBLICATIONS

Pub Med—Expert Opin Investig Drugs Apr. 8, 1999(4) 463-71-Metrifonate (Trichlorfon): a review of the pharmacology, pharmacokinetics and clinical experience with a new acetylcholinesterase inhibitor for Alzheimer's disease.—Ringman JM, Cummings, JL.

Pub Med. J. Microencapsul. Feb. 22, 2005(1) 57-66—Effects of formulation factors on encapsulation efficiency and release behaviour in vitro of huperzine A-PLGA microspheres—Fu X, Ping Q, Gao Y.

Journal of Chromatography 272 (1983) 216-220—Analysis of plasma physostigmine concentrations by liquid chromatography—Robin Whelpton.

Arch Neurol/vol. 58, Mar. 2001—Open-Label, Multicenter, phase 3 extension study of the safety and Efficacy of Donepezil in Patients with Alzheimer Disease—Rachelle S. Doody MD -p. 427-433.

The Effects of Donepezil in Alzheimer's Disease-Results from a Multinational Trial—Derment Geriatr Cogn Disord 1999; 10: 237-244—A. Burns.

International Journal of Chronobiology, vol. 2, 281-289 (1974)—Circadian Variations of Acetylcholinesterase (E.C.3.1.1.7) in Rats Brains 0 H. Schiebeler and H. v. Mayersbach.

Neuroscience Letters 300 (2001) 157-160—Differential increase in cerebrospinal fluid-acetylcholinesterase after treatment with acetylcholinesterase inhibitors in patients with Alzheimer's disease—Pia Davidsson.

Brain Research, 122 (1977) 562-267—The time-dependent induction of REM sleep and arousal by physostigmine infusion during normal human sleep—Natarajan Sitaram.

JAGS—Jan. 1998—vol. 46, No.—p. 119-120-Aricept-induced nightmares in Alzheimer's Disease.

Tariot P, Gaile SE, Castelli NA, Porsteinsson AP, Treatment of agitation in dementia. New Dir Ment Health Serv 1997; 76: 109-23.

Devanand DP, Behavioral complications and their treatment in Alzheimer's disease, Geriatrics 1997; 52:Suppl 2:S37-39.

Jacobsen FM and Comas-Dias L, Donepezil for psychotropic-induced memory loss, J Clin Psychiatry Oct. 1999;60( 10):698-704.

CummingsJ L, Mendez MF, Alzheimer's disease: cognitive and behavioral pharmacotherapy. Conn Med 1997; 61:543-552.

Cummings JL, Changes in neuropsychiatric symptoms as outcome . . . cholinergic therapies for Alzheimer disease. Alzheimer Dis Assoc Disord 1997; 11 Suppl 4:S1-9.

Cummings JL, Back C, The cholinergic hypothesis of neuropsychiatric symptoms in Alzheimer's disease. Am J Geriatr Psychiatry 1998; 6(2Suppl 1):S64-78.

Rogers SL, Farlow MR, Doody RS, Mohs R, Friedhoff LT, et al, A 24-week, double-blind, placebocontrolled trial of donepezil in patients with Alzheimer's disease. Neurology 1998; 50:136-145.

Cummings J, Winblad B, A rivastigmine patch for the treatment of Alzheimer's disease and Parkinson's disease dementia. Expert Rev Neurother 2007; 7: 1457-63.

Witting W, Kwa IH,Eikelenbloom P, Mirrniran M, Swaab DF, Alterations in the circadian rest-activity rhythm in aging and Alzheimer's disease. Biol Psychiatry 1990; 7563-72.

Tate B, Aboody-Guterman KS, Morris AM, Walcott EC, Majocha RE, Marotta CA, Disruption of . . . Proc Natl Acad Sci USA 1992;89:7090-4.

Mishirna K, Okawa M, Satoh K, Shimizu T, Hozumi S, Hishikawa Y, Different manifestations of circadian . . . Neurobiol Aging 1997; 18:105-9.

Van Someren EJ, Scherder EJ, Swaab DF, Transcutaneous electrical nerve stimulation (TENS) improves . . . Dis Assoc Disord 1998; 12: 114-8.

Satlin A, Volicer L, Ross V, Herz L, Campbell S, Bright light treatment of behavioral and sleep disturbances in patients with Alzheimer's disease. Am J Psychiatry 1992; 149: 1028-32.

Satlin A, Volicer L., Stopa EG, Harper D, Circadian locomotor activity and core-body temperature rhythmsin Alzheimer's disease. Neurobiol Aging 1995; 16:765-71.

Van Someren EJ, Habebeuk EE, Lijzenga C, Scheltens P, de Rooij SE, Jonker C, Pot AM, . . . disease. Biol Psychiatry 1996; 40:259-70.

Saito Y, Yamashita I, Yamazaki K, Okada F, Satorni R, Fujieda T, Circadian fluctuation of . . . brain areas. Life Sci 1975; 16:281-288.

Reimann D, Gann H, Dressing H, Muller WE, Aldenhoff JB, Influence of the cholinesterase inhibitor . . . sleep. Psychiatry Res 1994; 51:253-267.

Morley BJ, Murrin LC, AF64 depletes hypothalamic high-affinity choline uptake and . . . receptors. Brain Res1989; 504:238-246.

Szymusiak R, McGinty D, Fairchild MD, Jenden DJ, Sleep-wake disturbances . . . Brain Res 1993; 629:141-145.

Von der Kammer H, Mayhaus M, Albrecht C, Enderich J, Wegner M, Nitsch RM, Muscarinic . . . factors. J Biol Chem 1998; 273:14538-14544.

Davidsson P, Blennow K, Andreasen N, Eriksson B, Minthon L, Hesse C, Differential . . . disease, Neuroscience Letters 2001 ; 300: 157-160.

Nordberg A, Hellstrom-Lindahl E, Almkvist O, Meurling L, Activity of acetylcholinesterase in CSF . . . Alzheimer's Reports 1999; 2:347-352.

Doody RS, Geldmacher DS, Gordon B, Perdomo CA, F'ratt RD, et al, Open-label, multicenter, phase 3 . . . Arch Neurol 2001; 58:427-433.

Stern RG, Mohs RC, Davidson M, Schmeidler J, Silverman J, Kramer-Ginsberg E, Searcey T, Bierer L, . . . Psychiatry 1994; 151:390-396.

Raskind MA, Peskind ER, Truyen L, Kershaw P, Damaraju CRV, The cognitive benefits . . . trial. Arch Neurol 2004; 61:252-256.

Remington, The Science and Practice of Pharmacy (21$^{st}$ Edition, 2006) pp. 939-964.

Modem Pharmaceutics (2$^{nd}$ Edition 1990), Chapter 16 "Sustained and Controlled-Release Drug Delivery Systems" pp. 635-671).

Tiseo, P. J., et al. "Pharmacokinetic and Pharmacodynamic Profile of Donepezil HC1 Following Evening Administration" Br J Clin Pharmacol 1998: 46 (Suppl. 1): 13-18.

Sherman, K. A. "Pharmacodynamics of Oral E2020 and Tacrine in Humans: Novel Approaches" in Cholinergic Basis for Alzheimer Therapy, R. Becker and E. Giacobin, eds., Birkhauser Boston, 1991, pp. 321-328.

Burns, A. et al. "The Effects of Donepezil in Alzheirner's's Disease—Results from a Multinational Trial" Dement Geriatr Cogn Disord 1999.

Doody, Rachelle S. et al. "Open-Label, Multicenter, Phase 3 Extension Study of the Safety and Efficacy of Donepezil in Patients With Alzheimer Disease" Arch Neurol 2001; 58:427-433.

Burns, A. et al. "Efficacy and safety of Donepezil Over 3 Years: An Open-Label, Multi-Centre Study in Patients with Alzheimer's Disease" Int J Geriatr Psychiatry 2007; 22:806-12.

Morris, J.C. et al "Cognitive Benefits of Long-Term, Continuous Galantamine Treatment in Patients with Alzheimer's Disease" Poster presented at the 7$^{th}$ International Geneva/Springfield Symposium on Advances in Alzheimer Therapy, Geneva, Switzerland, Apr. 3-6, 2002.

Rogers, S.L. "A 24-Week. Double-Blind. Placebo-Controlled Trial on Donepezil" Neurology, vol. 50, pp. 136-145, 1998.

Vanmechelen, E. et al. "Effect of Cholinesterase Inhibitors on Alzheimer's Disease Biomarkers" Poster presented at 8$^{th}$ International Conference on Alzheimer's Disease and Related Disorders (ICAD), Stockholm, Sweden, Jul. 2002.

Geldmacher, David S. et al. "Donepezil Is Associated with Delayed Nursing Home Placement in Patients with Alzheimer's Disease" J Am Geriatr Soc 2003: 51:937-944.

Johannsen, Peter, et al. "Assessing Therapeutic Efficacy in a Progressive Disease: A Study of Donepezil in Alzheimer's Disease" CND Drugs 2006: 20:311-325.

Rees, T. et al. "Acetylcholinesterase Promotes Beta-Amyloid Plaques in Cerebral Cortex" Neurobiology of Aging 2003: 24:777-787.

Chiao, C.S.L., et al. "Sustained-Release Drug Delivery Systems," Remington: The Science and Practice of Pharmacy, Gennaro, A.R., ed. 1995, pp. 1660 & 1661.

* cited by examiner

DOSAGE FORMULATIONS FOR ACETYLCHOLINESTERASE INHIBITORS

FIELD OF THE INVENTION

The present invention relates to dosage forms for cholinesterase inhibitors that will assist in obviating some of the undesirable side effects of use of such drugs and in methods of administering such drugs for this purpose.

BACKGROUND OF THE INVENTION

Recently there has been considerable interest in the use of several drugs in this class including tacrine, donepezil, physostigmine, rivastigmine and galanthamine for the treatment of Alzheimer's disease. Cholinergic drugs are known to have an effect on the body's circadian rhythms and in U.S. Pat. No. 5,585,375, I have claimed the use of galanthamine for treatment of jet lag. Although beneficial in some respects, circadian effects of cholinergic drugs may cause problems for care givers in cases where the patient is unable to take care of his or herself since it can result in the patient becoming active and needing attention during the night.

SUMMARY OF THE INVENTION

The object of the present invention is to time the release of acetylcholinesterase-inhibiting medication so as to provide it on a suitable physiological schedule, for example to ensure that it can be taken while a patient is awake in the evening and will be acting at the time of expected awakening in the morning and to provide dosage forms suitable for this purpose.

From a first aspect, the present invention provides dosage forms of a pharmaceutical composition which comprise an effective amount of an acetylcholinesterase inhibitor wherein the acetylcholinesterase inhibitor is formulated so as to delay its activity for a specified period. For example in one aspect such delay will be for a period of four to twelve hours so that a dose may be administered to the patient in the evening and allow a night's sleep before the acetyl cholinesterase inhibitor becomes active in the morning. The duration of delay chosen will depend upon the exact way in which it is chosen to administer the drug. For example if it is intended to administer the drug with an evening meal taken at, say 6:30 in the evening a twelve hour delay may be appropriate if one wishes the drug to be active the following morning. If the desired time of administration is bed time, however, a six or seven hour delay may be more useful.

From a second aspect, the present invention provides a method of treatment of a patient suffering from a disease or condition in which it is desirable to administer a centrally acting acetylcholinesterase inhibitor, such as Alzheimer's disease, which comprises administering a dosage form of a pharmaceutical composition which comprises an effective amount of an acetylcholinesterase inhibitor wherein the acetylcholinesterase inhibitor is formulated so as to delay its activity for a specified period prior to acetylcholinesterase inhibition being desired.

DETAILED DESCRIPTION OF THE INVENTION

Acetylcholinesterase inhibitors of use in the present invention are those that have a central effect and have a medium duration of action (typically from 2 to 12 hours) for the treatment of diseases where acetylcholinesterase inhibiting activity in the brain is desired, especially in the treatment of Alzheimer's disease. Suitable acetylcholinesterase inhibitors will typically have a half life in the body of from 1 to 11 hours and once released from the dosage form will pass easily through the blood-brain barrier. The most suitable compounds for this purpose are galanthamine, lycoramine and their analogs wherein at least one of the methoxy, hydroxy or methyl groups of the galanthamine or lycoramine is replaced as follows:

the methoxy group by another alkoxy group of from one to six carbon atoms, a hydroxy group, hydrogen, an alkanoyloxy group, a benzoyloxy or substituted benzoyloxy group, a carbonate group or a carbamate group;

the hydroxy group by an alkoxy group of from one to six carbon atoms, hydrogen, an alkanoyloxy group, a benzoyloxy or substituted benzoyloxy group, a carbonate group or a carbamate group;

the N-methyl group by hydrogen, alkyl, benzyl, cyclopropylmethyl group or a substituted or unsubstituted benzoyloxy group.

When reference is made to a substituent group, said group may be selected from alkyl or alkoxy groups of from 1 to 6 carbon atoms, halo groups, and haloalkyl groups such as trifluoromethyl.

One or more of the methoxy, hydroxy and methyl groups of galanthamine or lycoramine may be replaced by the groups noted above.

Galanthamine and lycoramine have the following formulae:

Galanthamine

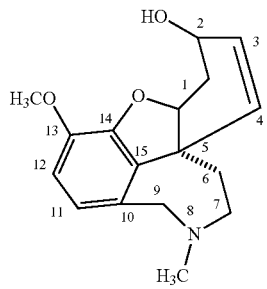

Lycoramine

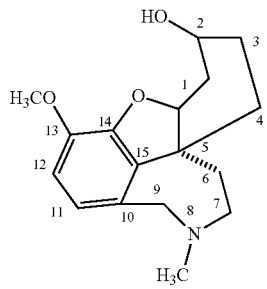

Suitable analogs are described for example in International Patent Publication WO88/08708 and an article by Bores and Kosley in Drugs of the Future 21: 621-631 (1996). Other useful pharmacologic agents for such preparations include rivastigmine, and other pharmacologic agents with half lives of 1-11 hours.

Particularly useful analogs of galanthamine and lycoramine that are of use in the present invention include analogs thereof wherein the methoxy group of such compounds is replaced by a hydrogen, hydroxy or alkoxy group of from two to six carbon atoms or an acyloxy group, for example an alkanoyloxy or benzoyl group, of from one to seven carbon atoms or where methoxy group thereof is replaced by a mono or dialkyl carbamate or carbonate group wherein the alkyl groups contain from 1 to 8 carbon atoms, preferably of from 4 to 6 carbon atoms or wherein the methoxy group thereof is replaced by an aryl carbamate or carbonate group wherein said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups.

Other useful analogs include compounds wherein, independently of whether or not the methoxy group has been replaced, the hydroxy group is replaced by an alkoxy group of from one to six carbon atoms, hydrogen, an acyloxy group, for example an alkanoyl oxy group, typically of from 1 to 7 carbon atoms, a benzoyloxy or substituted benzoyloxy group wherein said substituent is selected from alkyl and alkoxy groups of from 1 to 6 carbon atoms, trifluoro methyl groups and halo groups, a carbonate group or a carbamate group which may be a mono or dialkyl or an aryl carbamate or carbonate wherein the alkyl groups contain from 1 to 8 carbon atoms, preferably of from 4 to 6 carbon atoms or said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups.

Although a major use of the present invention will be in the treatment of Alzheimer's disease, it is also suitable for treatment of other diseases or conditions in which there is need for increased brain acetyl choline levels after a defined period. Thus it may find use, for example for healthy persons who have need for increased acetyl choline levels some specified time in the future, for example workers changing from a day shift to a night shift or vice-versa.

In Alzheimer's disease, the primary and universal neurochemical abnormality is a deficit of acetylcholine. The normal pattern of brain acetylcholine is elevated release just before and during the time of activity, and reduced release during sleep. (Kametani, 1991; Mizuno, 1991) The brain content of acetylcholine exhibits a reciprocal relationship with release patterns, presumably representing stored neurotransmitter. (Saito, 1974) Likewise, acetylcholinesterase activity, which keeps synaptic acetylcholine concentrations low, peaks during the subjective night, and is lowest during activity periods. (Schiebeler, 1974) Consistent with these experimental results is the long-recognized diurnal variation of human bronchial constriction from acetylcholine inhalation, being most sensitive in the evening, when endogenous cholinergic activity would be expected to be low, and least sensitive during waking hours, when cholinergic systems would be expected to be active (Reinberg, 1974) Humans are also sensitive to the systemic administration of the acetylcholinesterase inhibitors, physostigmine and galanthamine late in the day or at night, when endogenous cholinergic activity is low. These disturb sleep and produce awakenings. (Sitaram, 1979, Reimann, 1994)

Animals who are made hypocholinergic either by disruption of the high affinity choline uptake system or by being raised on a false cholinergic neurotransmitter have a reduced circadian variation of acetylcholine and a disrupted diurnal rhythm of locomotor activity, which correlates with the cholinergic hypoactivity. (Morley 1989, Szymusiak, 1993) This same situation exists in Alzheimer patients who have both cholinergic deficits and disruption of normal sleep-wake cycles. It is of major practical importance because a patient who requires twenty-four hour supervision wears out a single caretaker, requiring multiple shifts of caretakers, or institutionalization, which is expensive, frightening to the patient, and sad for the family. (see New York Times article, Jul. 27, 1998) An additional potential utility of a dosage form which can be taken when convenient, and active when needed, would therefore be the superimposition of a physiological rhythm of cholinergic activity, via a pill, onto a brain in which the cholinergic system is deteriorating.

Preparations for treatment of Alzheimer's disease, containing cholinomimetic agents, may stimulate intestinal peristalsis as they are released, thus promoting their own passage through the gastrointestinal tract. In may therefore be useful to incorporate into the dosage unit, or to manufacture a second, similarly timed tablet, to deliver an anticholinergic agent designed to remain outside the blood brain barrier, in order to reduce gastrointestinal motility. The anticholinergic tablet might contain, for example, probanthine, 7.5-60 mg, or robinul 1 to 8 mg. A desirable formulation for an Alzheimer patient for whom sleeping hours of 11 pm to 7 am are desirable might be a pill which could be taken at bedtime and begin to release galanthamine at 5 am at a rate of 3 mg (measured as base) per hour for 4 hours, or 2 mg/hour for 6 hours beginning at 4 am. The same pill, taken at 7 am, would cover the daytime hours. This should allow the central nervous system to become relatively hypocholinergic at the time of desired sleep, as the half life of galanthamine has been reported to be 4.5-8 hours. (Thomsen, 1990)

Alternatively, a single pill may deliver a full day's medication, although there is some risk of dumping an excessive dose, which could be dangerous in the case of cholinergic medications. The delay before release of active medication could be chosen between one and 11 hours depending on whether the pill is to be taken at dinner or bedtime.

Likely pharmacologic agents for such preparations include galanthamine, rivastigmine, and other pharmacologic agents with half lives of 1-11 hours. Dosage units for twice daily administration should contain from 4-16 mg of galanthamine (as base), or 2-10 mg of rivastigmine, both of which should be doubled in the case of once per day dosage units. Dosages for other suitable agents can be determined by standard techniques such as those set out for example in Chapter 6 (by Benjamin Calesnick) of Drill's Pharmacology in Medicine (Fourth Edition Joseph R DiPalma ed, McGraw-Hill 1971 or in Chapter 6 (by B. E. Rodda et al) of Biopharmaceutical Statistics for Drug Development (ed. Karl E. Peace, Marcel Dekker Inc, 1988). Anticholinergic agents, if needed, could be probanthine, 7.5-60 mg, to be delivered at the same time as the cholinomimetic agents, or robinul (1 to 8 mg) or similar agents incorporated so that a typical dose is delivered within the time frame of the cholinomimetic release.

Delayed action formulations for use in the present invention typically are those used for oral administration and include tablets, capsules, caplets and other convenient devices. Such dosage units may be prepared by methods well known to those skilled in the art, such as those described in Sustained Release Medications by J. C. Johnson, Noyes Data Corporation, 1980, and an article by Conte et al in Biomaterials 1993 vol 14 pages 1017 to 1023 entitled Press-coated tablets for time-programmed release of drugs, both of which are incorporated herein by reference. For example the active compounds may be coated or incorporated in a matrix which controls the elapse of between administration of the dose and the time at which release is desired.

What I claim is:

1. A dosage form of a pharmaceutical composition which comprises an effective amount of a centrally-acting acetylcholinesterase inhibitor for the treatment of Alzheimer's disease selected from the group consisting of rivastigmine, galanthamine, lycoramine, analogs of galanthamine, and analogs of lycoramine wherein said analogs of galanthamine or lycoramine are compounds wherein one or more of the methoxy, hydroxy or N-methyl groups is replaced as follows: the methoxy group by another alkoxy group of from two to six carbon atoms, a hydroxy group, hydrogen, an alkanoyloxy group, a benzoyloxy or substituted benzoyloxy group, a carbonate group or a carbamate group; the hydroxy group by an alkoxy group of from one to six carbon atoms, hydrogen, an alkanoyloxy group, a benzoyloxy or substituted benzoyloxy group; a carbonate group or a carbamate group; the N-methyl group by hydrogen, alkyl, benzyl or a cyclopropylmethyl group or a substituted or unsubstituted benzoyloxy group; said centrally-acting acetylcholinesterase inhibitor having a half life of from one to eleven hours wherein the acetylcholinesterase inhibitor is formulated so as to delay its activity for a predetermined period of from four to twelve hours such that acetyl-cholinesterase inhibition is avoided during such predetermined period.

2. A dosage form of a pharmaceutical composition as claimed in claim 1 wherein the composition is formulated to delay the activity of the acetyl-cholinesterase inhibitor for a period of from six to nine hours.

3. A dosage form of a pharmaceutical composition as claimed in claim 1 wherein the composition is formulated to delay the activity of the acetyl-cholinesterase inhibitor for a period of from eight to twelve hours.

4. A dosage form of a pharmaceutical composition as claimed in claim 1 wherein said acetylcholinesterase inhibitor has a duration of action of from 2 to 12 hours.

5. A dosage form as claimed in claim 1 wherein said acetylcholinesterase inhibitor is selected from the group consisting of galanthamine, lycoramine and analogs thereof wherein the methoxy group of such compounds is replaced by a hydrogen, hydroxy or alkoxy group of from two to six carbon atoms or an acyloxy group of from one to seven carbon atoms.

6. A dosage form as claimed in claim 1 wherein said acetylcholinesterase inhibitor is selected from the group consisting of analogs of galanthamine or lycoramine wherein the methoxy group thereof is replaced by a mono or dialkyl carbamate or carbonate group wherein the alkyl groups contain from 1 to 8 carbon atoms.

7. A dosage form as claimed in claim 6 wherein the alkyl group or groups of said carbonate or carbamate groups comprise from 4 to 6 carbon atoms.

8. A dosage form as claimed in claim 1 wherein said acetylcholinesterase inhibitor is selected from the group consisting of analogs of galanthamine or lycoramine wherein the hydroxy group thereof is replaced by a mono or dialkyl carbamate or carbonate group wherein the alkyl groups contain from 1 to 8 carbon atoms.

9. A dosage form as claimed in claim 7 wherein the alkyl group or groups of said carbonate or carbamate groups comprise from 4 to 6 carbon atoms.

10. A dosage form as claimed in claim 1 wherein said acetylcholinesterase inhibitor is selected from the group consisting of analogs of galanthamine or lycoramine wherein the methoxy group thereof is replaced by an aryl carbamate or carbonate group wherein said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups.

11. A dosage form as claimed in claim 1 wherein said acetylcholinesterase inhibitor is selected from the group consisting of analogs of galanthamine and lycoramine wherein the hydroxy group thereof is replaced by an aryl carbamate or carbonate group wherein said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups.

12. A dosage form as claimed in claim 1 wherein said acetylcholinesterase inhibitor is selected from the group consisting of galanthamine, lycoramine and analogs thereof wherein the hydroxy group of such compounds is replaced by a hydrogen or alkoxy group of from one to six carbon atoms or an acyl group of from one to seven carbon atoms.

13. A dosage form of a pharmaceutical composition as claimed in claim 1 wherein said acetylcholinesterase inhibitor is selected from the group consisting of analogs of galanthamine and lycoramine wherein the hydroxy group of galanthamine or lycoramine is replaced by an alkoxy group of from one to six carbon atoms, hydrogen, an alkanoyloxy group, a benzoyloxy or substituted benzoyloxy group, a carbonate group or a carbamate group.

14. A dosage form as claimed in claim 1 wherein said acetylcholinesterase inhibitor is galanthamine.

15. A dosage form as claimed in claim 1 wherein said acetylcholinesterase inhibitor is rivastigmine.

16. A method of treatment of a patient suffering from Alzheimer's disease which comprises administering a delayed release dosage form of a pharmaceutical composition which comprises an effective amount for treating Alzheimer's disease of a centrally acting acetycholinesterase inhibitor selected from the group consisting of rivastigmine, galanthamine, lycoramine, analogs of galanthamine, and analogs of lycoramine wherein said analogs of galanthamine or lycoramine are compounds wherein one or more of the methoxy, hydroxy or N-methyl groups is replaced as follows: the methoxy group by another alkoxy group of from two to six carbon atoms, a hydroxy group, hydrogen, an alkanoyloxy group, a benzoyloxy or substituted benzoyloxy group, a carbonate group or a carbamate group; the hydroxy group by an alkoxy group of from one to six carbon atoms, hydrogen, an alkanoyloxy group, a benzoyloxy or substituted benzoyloxy group, a carbonate group or a carbamate group; the N-methyl group by hydrogen, alkyl, benzyl or a cyclopropylmethyl group or a substituted or unsubstituted benzoyloxy group; wherein said dosage is formulated such that the half life of the activity of the acetylcholinesterase inhibitor and the degree of delayed release are selected such that the formulation may be administered to the patient such that release of acetyl-cholinesterase inhibitor is avoided for the next anticipated sleep time and wherein administration of the drug is at an appropriate time to achieve such results.

17. A method of treatment as claimed in claim 16 wherein the composition is formulated to delay release of the acetyl cholinesterase inhibitor for a period of from six to nine hours.

18. A method of treatment as claimed in claim 16 wherein the composition is formulated to delay release of the acetyl cholinesterase inhibitor for a period of from eight to twelve hours.

19. A method of treatment as claimed in claim 16 wherein said acetylcholinesterase inhibitor has a duration of action of from 2 to 12 hours.

20. A method of treatment as claimed in claim 16 wherein said acetylcholinesterase inhibitor is selected from the group consisting of galanthamine, lycoramine and analogs thereof wherein the methoxy group of such compounds is replaced by a hydrogen, hydroxy or alkoxy group of from two to six carbon atoms or an acyloxy group of from one to seven carbon atoms.

21. A method of treatment as claimed in claim 16 wherein said acetylcholinesterase inhibitor is selected from the group consisting of analogs of galanthamine or lycoramine wherein the methoxy group thereof is replaced by a mono or dialkyl carbamate or carbonate group wherein the alkyl groups contain from 1 to 8 carbon atoms.

22. A method of treatment as claimed in claim 21 wherein the alkyl group or groups of said carbonate or carbamate groups comprise from 4 to 6 carbon atoms.

23. A method of treatment as claimed in claim 22 wherein said acetylcholinesterase inhibitor is selected from the group consisting of analogs of galanthamine or lycoramine wherein the hydroxy group thereof is replaced by a mono or dialkyl carbamate or carbonate group wherein the alkyl groups contain from 1 to 8 carbon atoms.

24. A method of treatment as claimed in claim 23 wherein the alkyl group or groups of said carbonate or carbamate groups comprise from 4 to 6 carbon atoms.

25. A method of treatment as claimed in claim 16 wherein said acetylcholinesterase inhibitor is selected from the group consisting of analogs of galanthamine or lycoramine wherein the methoxy group thereof is replaced by an aryl carbamate or carbonate group wherein said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups.

26. A method of treatment as claimed in claim 16 wherein said acetylcholinesterase inhibitor is selected from the group consisting of analogs of galanthamine and lycoramine wherein the hydroxy group thereof is replaced by an aryl carbamate or carbonate group wherein said aryl group is selected from phenyl, naphthyl, substituted phenyl and substituted naphthyl groups wherein said substituent is selected from alkyl and alkoxy groups of from 1 to 6 carbon atoms, trifluoro methyl groups and halo groups.

27. A method of treatment as claimed in claim 16 wherein said acetylcholinesterase inhibitor is selected from the group consisting of galanthamine, lycoramine and analogs thereof wherein the hydroxyl group of such compounds is replaced by a hydrogen or alkoxy group of from one to six carbon atoms or an acyl group of from one to seven carbon atoms.

28. A method of treatment as claimed in claim 16 wherein said acetylcholinesterase inhibitor is galanthamine.

29. A method of treatment as claimed in claim 16 wherein said acetylcholinesterase inhibitor is rivastigmine.

30. A method of treatment as claimed in claim 16 wherein said acetylcholinesterase inhibitor is administered in conjunction with a compound that reduces its peripheral effects.

31. A method of treatment as claimed in claim 30 wherein said acetylcholinesterase inhibitor is administered in conjunction with a suitable dose of propantheline bromide or glycopyrrolate.

32. A method of treating Alzheimer's disease comprising administration to a patient suffering therefrom a composition comprising a centrally acting acetyl-cholinesterase inhibitor selected from the group consisting of rivastigmine, galanthamine, lycoramine, analogs of galanthamine, and analogs of lycoramine wherein said analogs of galanthamine or lycoramine are compounds wherein one or more of the methoxy, hydroxy or N-methyl groups is replaced as follows: the methoxy group by another alkoxy group of from two to six carbon atoms, a hydroxy group, hydrogen, an alkanoyloxy group, a benzoyloxy or substituted benzoyloxy group, a carbonate group or a carbamate group; the hydroxy group by an alkoxy group of from one to six carbon atoms, hydrogen, an alkanoyloxy group, a benzoyloxy or substituted benzoyloxy group, a carbonate group or a carbamate group; the N-methyl group by hydrogen, alkyl, benzyl or a cyclopropylmethyl group or a substituted or unsubstituted benzoyloxy group; said compounds having a half life of from one to eleven hours wherein the nature of the composition and the time of administration of said acetyl cholinesterase inhibitor from said composition is such as to minimize release prior and during desired sleep hours so as to allow the patient's central nervous system to become hypocholinergic during the period of desired sleep as compared to its cholinergic activity during hours when desired to be awake SO as to superimpose a physiological rhythm of cholinergic activity to a brain in which the cholinergeic system is deteriorating.

* * * * *